United States Patent [19]

Takagi et al.

[11] Patent Number: 4,610,962

[45] Date of Patent: Sep. 9, 1986

[54] CARRIERS FOR IMMOBILIZATION OF PHYSIOLOGICALLY ACTIVE SUBSTANCES

[75] Inventors: Kunihiko Takagi, Kyoto; Masatsugu Mochizuki, Shiga; Izumi Sakamoto; Hiroichi Teranishi, both of Kyoto, all of Japan

[73] Assignee: Unitika Ltd., Hyogo, Japan

[21] Appl. No.: 616,511

[22] Filed: Jun. 1, 1984

[30] Foreign Application Priority Data

Jun. 3, 1983 [JP] Japan ................... 58-99872

[51] Int. Cl.$^4$ ............... C12N 11/12; C12N 11/08; G01N 33/544; C08B 16/00
[52] U.S. Cl. ................... 435/179; 435/177; 435/180; 435/182; 436/530; 428/378; 428/507; 428/508; 428/510; 428/527; 428/537.5; 536/63; 536/57
[58] Field of Search ............... 435/179, 180, 182, 177; 436/530; 428/527, 537.5, 378, 507, 508, 510; 536/63, 57

[56] References Cited

U.S. PATENT DOCUMENTS 3,764,477  10/1973  Lehmann et al. ............... 435/180
3,849,253  11/1974  Harvey et al. ............... 435/182
4,063,017  12/1977  Tsao et al. ............... 536/57
4,115,198   9/1978  Coughlin et al. ............... 435/176
4,356,267  10/1982  Callegaro et al. ............... 435/179
4,378,435   3/1983  Takagi et al. ............... 435/180

FOREIGN PATENT DOCUMENTS 0424242  5/1933  United Kingdom ............... 536/57

*Primary Examiner*—Sidney Marantz
*Assistant Examiner*—L. Krawczewicz
*Attorney, Agent, or Firm*—Sughrue, Mion, Zinn, Macpeak and Seas

[57] ABSTRACT

A carrier for immobilization of physiologically active substances is prepared by treating an assembly of regenerated cellulose fibers having a single fiber fineness of from 0.5 to 30 deniers and a length of at least 1 millimeter with a solution of a polymer having an acid anhydride group. This carrier is easy to handle and permits immobilization of a large amount of a physiologically active substance. Thus it can be used as a catalyst for chemical reactions, a specific absorbent for separation and purification, a material for clinical examination, or a medical material.

21 Claims, No Drawings

CARRIERS FOR IMMOBILIZATION OF PHYSIOLOGICALLY ACTIVE SUBSTANCES

FIELD OF THE INVENTION

The present invention relates to carriers for use in immobilization of physiologically active substances.

BACKGROUND OF THE INVENTION

Physiologically active substances such as enzymes, coenzymes, enzyme inhibitors, hormones, antibacterial agents, antigens and antibodies which are immobilized on a carrier such as polyacrylamide, cellulose, agarose, and glass are used as catalysts for chemical reactions, specific absorbents for separation and purification, materials for clinical examination, therapeutic materials, and so forth.

For example, Weliky et al. report immobilization of peroxidase on finely powered carboxymethylated cellulose by the use of dicyclohexylcarbodiimide (see N. Weliky, F. S. Brown and E. C. Dale, *Archives of Biochemistry and Biophysics*, Vol. 131, pages 1-8 (1969)). Cellulose is a preferred carrier in that functional groups capable of reacting with physiologically active substances (e.g., enzymes) under moderate conditions, such as carboxyl group and an epoxy group, can be introduced thereinto. However, cellulose in a fine powder form is difficult to handle and is not suitable for industrial use as a chemical reaction catalyst or specific absorbent for separation and purification.

Japanese Patent Application (OPI) No. 5393/77 (the term "OPI" as used herein means a "published unexamined Japanese patent application") discloses that a carrier prepared by carboxyalkylation of a molded cellulose is suitable for use in adsorption of physiologically active substances such as urokinase. This carrier, however, fails to immobilize physiologically active substances by means if a covalent bond when used without modification. Furthermore, the amount of the substance being immobilized cannot be expected to increase to a satisfactory level.

SUMMARY OF THE INVENTION

The object of the present invention is to provide carriers for immobilization of physiologically active substances which are easy to handle and further which are capable of easily immobilizing a large quantity of physiologically active substances.

It has been found according to the present invention that an assembly of activated regenerated cellulose fibers prepared by treating an assembly of regenerated cellulose fibers having a single fiber fineness of from 0.5 to 30 deniers and a length of at least 1 millimeter with a solution of a polymer having an acid anhydride group, when used as a carrier for immobilization of physiologically active substances, are free from irregularities in shape which occur in the case of natural cellulose fibers, are easy to handle, and which are capable of immobilizing the substances with ease and in large amounts.

Thus the present invention is directed to a carrier for immobilization of physiologically active substances which is prepared by treating an assembly of regenerated cellulose fibers having a single fiber fineness of from 0.5 to 30 deniers and a length of at least 1 millimeter with a solution of a polymer having an acid anhydride group.

DETAILED DESCRIPTION OF THE INVENTION

The term "cellulose" as used herein means a polysaccharide composed of glucose units connected by the $\beta$-1,4-glucocidic linkage.

The term "regenerated cellulose" as used herein means a cellulose which is prepared by dissolution and regeneration of pulp derived from a plant starting material. This includes viscose rayon, cuprammonium rayon, and saponificated acetate. These regenerated celluloses can be prepared by known procedures. Therefore, the regenerated cellulose as used herein can be prepared so as to have any desired single fiber fineness and also any desired length, unlike natural cellulose. Thus, when the carrier of the present invention is used, for example, as a column filler, it can be shaped into such a form as to prevent plugging.

Physiologically active substances which are used in the present invention are substances that exert significant influences on physiological functions of animals and plants, such as enzymes, coenzymes, enzyme inhibitors, proenzymes, hormones, antibiotics, germicides, antitumor agents, and immunoreactive substances.

Examples of enzymes include oxidoreductases such as alcohol dehydrogenase, lactate dehydrogenase, glucose-6phosphate dehydrogenase, glucose oxidase, luciferase, L-amino-acid oxidase, catalase, tyrosinase, and peroxidase; transferases such as hexokinase, pyruvic acid dehydrogenase, carbamatekinase, acetatekinase, and ribonuclease; hydrolases such as lipase, acetylcholinesterase, steroidesterase, amylase, cellulase, dextranase, invertase, pepsin, renin, trypsin, chymotripsin, papain, ficin, thrombin, kallikreins, streptokinase, urokinase, plasmin, plinolase, asparakinase, urease, penicillinamydase, and apilase; lyases such as pyruvic acid decarboxylase, alpartase, and threonine deamylase; isomerases such as glucose isomerase; and ligases such as tyrosyl-TRNA synthetase and acetyl-CoA synthetase.

Examples of coenzymes include pyridoxal phosphate and nicotine adeninedinucleotide.

Examples of enzyme inhibitors include ovomucoid, Kunitz soy bean trypsin inhibitors, aprotinin, antitrobin III, $\alpha_2$-macroglobin, $\alpha_1$-antitrypsin, $\alpha_1$-antiplasmin, plasminogen antiactivators, and heparin.

Examples of proenzymes include plasminogen, fibrinogen, prothrombin, and blood clotting factor XIII.

Examples of hormones include cortisone, testosterone, estrone, estradiol, progesterone, insulin, somastatin and gonadotropin.

Examples of antibiotics include penicillins such as cloxacillin, cycroxacillin, flucloxacillin, ampicillin, hetacillin, talampicillin, cyclacillin, amoxillin, pivmecillinam and piperacillin; cephalosporins such as cephaloridine, cephaloglycin, cephalexin, cephazolin, cephapyrin, cephradine, cephrazole, cefoxitin and cefatrizine; aminoglycosides such as streptomycin, kanamycin, fradiomycin, paromomysin, gentamycin, bekamamycin, ribostamycin, dibekacin, amikacin, tobramycin and spectinomycin; tetracyclines such as oxytetracycline, tetracycycline, dimethylchlorotetracycline, metacycline, doxycycline and minocycline; macrolides such as erythromycin, kitasamycin, oleandomycin, spiramycin, jasamycin and midecamycin; lincomycins such as lincomycin and clindamysin; anti-gram-positive bacteria such as mikamycin, gramicidin S and gramicidin; polymyxims such as colistin and polymyxin B; antimycobacteria such as biomycin, capreomycin, enbiomycin and cycloserin; polyenemacrolide such as amphotericin B and pimaricin; rifampicin; pyrrolenitrin; mitomycin C, actinomycin; bleomycin; daunorubicin; doxorubicin; and neocarzinostatin.

Examples of germicides include dye preparations such as acrynol and acrilflavine, furan medical preparations such as nitrofurazone, quaternary ammonium salts such as benzalkonium chloride, benzethonium chloride, guanidium salts such as chlorhexidine, iodine complexes such as povidoneiodine, and amphoteric surface active agents such as alkyldiamino-ethylglycine hydrochloride.

Examples of antitumor agents include alkylating agents such as nitrogen mustard, nitromin, chlorambucil, cyclophosphamide, melphalan, uracil mustard, mannomustine, dopan, BCNU (N,N-Bis(2-Chloroethyl)-N-nitroso-urea); triethylene melamine thio-TEPA (1,1',1''-Phosphinothioylidynetrisaziridine, or tris (1-aziridinyl)-phosphine sulfide, Aza-TEPA, threnimone, improcuon, busulfan, dimethylmilelane, piposulfan, ethoglucide, epoxypropidine, epoxypiperazine, hexamethylmelamine, dibromomannitol and pipobroman; antimetabolites such as folic acid, aminopterin, methotrexate, guanine, 8-azaguanine, 6-mercaptopurine, azathioprine, uracil, 5-fluorouracil, cytarabine, azaserine and diazamycin; antibiotics such as actinomycin D, cyclomycin, mitomycin C, daunomycin, bleomycin, cromomycin and carzinophyllin; synthetic agents such as 5-HP and IQ-1; plant components such as thiotepa, cyclophosphamide, doxorubicin, daunorubicin and neocarzinostain; Hg-hematoporphyrine; Co-protoporphyrine; stillbestrol; hydroxyurea; procarbazine; methylglyoxal-bis-guanylhydrazone; and L-asparaginase.

Immunoreactive substances are those capable of forming immunological bonds, such as antigens and antibodies. Antigens are substances capable of inducing an antigen-antibody reaction. They generally include peptides, proteins, polysaccharides, glucoproteins, and steroids. Antibodies are proteins which are produced in vivo by stimulation of antigens and which bond specifically to the antigens. They are immunoglobulins in their chemical behavior. Examples of the immunological substances include microorganisms such as molds, yeasts, protozoans, and virus, and their immunologically active components, antibodies, serum components, toxins, hormones, enzymes, alkaloids, cells, tissue extracts, blood cells, lectin, etc. as separated from human being and animals and the like.

The expression "carrier for immobilization of physiologically active substances" as used herein means substances to which the above-described physiologically active substances can be immobilized by the treatments as described hereinafter, and which are not physiologically active by themselves but exhibit physiological activity when a physiologically active substance is immobilized thereon.

The expression "assembly of fibers" as used herein means assemblies of short or long fibers. Such as staples, spun yarns, nonwoven fabrics, fabrics, and knitted fabrics.

The single fiber fineness constituting the assembly of fibers is from 0.5 to 30 deniers and preferably from 1 to 20 deniers. The fiber length is at least 1 millimeter, preferably at least 5 millimeters and more preferably at least 20 millimeters. If the fineness is less than 0.5 denier, the strength of the resulting assembly of fibers is low, and furthermore it is difficult to produce fibers of such low fineness. On the other hand, if it is in excess of 30 deniers, the surface area per weight is reduced and thus only a small amount of physiologically active substance can be immobilized. If the fiber length is less than 1 millimeter, the resulting fiber assembly is difficult to handle, as in the case of fine powder.

In the present invention, an assembly of regenerated cellulose fibers as described above is required to be treated with a solution of a polymer having an acid anhydride group. As cellulose contains therein only a hydroxyl group of low reactivity, physiologically active substances cannot be immobilized thereon without some suitable modification. It may be considered to introduce functional groups such as an imidocarbonate group, an isocyanate group, an epoxy group, a formyl group, an acid chloride group, an amino group, a carboxyl group, a carboxyalkyl group, a diazonium group, and an azido group. Introduction of such functional groups, however, is inferior to the treatment of the present invention using a solution of a polymer having an acid anhydride group for the following reasons: (1) a sufficient amount of physiologically active substance cannot be immobilized; (2) when immobilization is desired to be attained by means of a covalent bond, other compounds, such as a dehydration concentration agent, are required to be used; (3) it is inevitably necessary to use reagents which may exert adverse influences on human bodies, in the introduction of the functional groups; (4) the reagents are difficult to handle; (5) the mechanical strength of fibers is seriously lowered by the treatment for introduction of the functional groups; and (6) physiologically active substances are inactivated by the treatment.

The treatment of an assembly of regenerated cellulose fibers with a solution of a polymer having an acid anhydride group according to the present invention will hereinafter be described in detail.

Polymer having an acid anhydride group as used herein include poly(carboxylic anhydrides) such as poly(maleic anhydride), poly(itaconic anhydride), poly(acrylic anhydride), and poly(methacrylic anhydride), and copolymers containing the foregoing poly(carboxylic anhydrides) as a constitutional unit, such as copolymers of maleic anhydride and aliphatic vinyl ethers (e.g., a maleic anhydride/methyl vinyl ether copolymer, a maleic anhydride/ethyl vinyl ether copolymer, and a maleic anhydride/butanediol divinyl ether copolymer), copolymers of maleic anhydride and olefin monomers (e.g., a maleic anhydride/ethylene copolymer, a maleic anhydride/propylene copolymer, and a maleic anhydride/isobutylene copolymer), copolymers of maleic anhydride and aromatic vinyl monomers (e.g., a maleic anhydride/styrene copolymer), and copolymers of maleic anhydride and aliphatic vinyl esters (e.g., a maleic anhydride/vinyl acetate copolymer).

The polymer having an acid anhydride group is dissolved in solvents such as methanol, ethanol, propanol, isopropanol, butanol, tetrahydrofuran, ethyl acetate, methyl acetate, benzaldehyde, formaldehyde, acetone, cyclohexanone, methyl ethyl ketone, mesytil oxide, diacetone alcohol, 2-pyrrolidone, N-methyl-2-pyrrolidone, N-vinyl-2-pyrrolidone, butyrolactone, acetic acid, dimethylformamide, and pyridine. These solvents can be used singly or in combination with each other. The concentration of the polymer having an acid anhydride group is preferably from about 0.1 to 30% by weight, and more preferably from 0.5 to 10% by weight, based on the weight of the solution. If desired, sulfuric acid, hydrochloric acid, acetic acid, and the like may be added as catalysts, in proportions of preferably from about 0.01 to 10% by weight, and more preferably from about 0.05 to 2% by weight, based on the weight of the solution.

The thus-prepared solution is used to treat the assembly of regenerated cellulose fibers. This treatment is carried out at a temperature of from 0° to 150° C., preferably at from 0° to 100° C., and more preferably at from 20° to 80° C. for a period of from about 10 minutes to 72 hours, and preferably for from about 30 minutes to 36 hours. At elevated temperatures, the treating time is from about 10 minutes to 24 hours, and preferably from 30 minutes to 10 hours.

The treatment can be performed by known procedures such the dip process, the spray process, and the coating process.

For the carrier of the present invention for immobilization of physiologically active substances, it is preferred that the acid anhydride group content per gram of the carrier (calculated as a carboxyl group) be from 0.0002 to 20 milliequivalents. More preferably, it is from 0.002 to 10 milliequivalents, and most preferably it is from 0.02 to 5 milliequivalents. If the acid anhydride group content (calculated as a carboxyl group) is less than 0.0002 milliequivalents, the capacity to immobilize physiologically active substances tends to drop. On the other hand, if it is in excess of 20 milliequivalents, the strength of the carrier tends to drop, or when the carrier is practically used, the acid anhydride-base polymer tends to be eluted. The acid anhydride group content, as described above, is expressed in terms of the carboxyl group content. In determining the acid anhydride group content, acid anhydride group contained in the carrier are hydrolyzed into carboxyl group which are then measured by the neutralization titration process.

For immobilizing a physiologically active substance on the carrier of the present invention, as prepared by treating an assembly of regenerated cellulose fibers with a solution of a polymer having an acid anhydride group, by means of a covalent bond, the substance is dissolved or dispersed in water or a mixed solvent of water and a solvent compatible with water, such as methanol, ethanol, propanol, acetone, tetrahydrofuran, dioxane, dimethylsulfoxide and dimethylformamide, and thereafter the carrier is treated with the above-prepared solution or dispersion. This treatment is carried out at a temperature of preferably from −20° to 100° C. and more preferably from 0° to 80° C., for a period of preferably from 5 minutes to 100 hours and more preferably from 10 minutes to 80 hours. In the treatment, in order to adjust the pH to preferably 2 to 12 and more preferably 4 to 10, buffers such as phosphate and acetate may be added, or hydrochloric acid, sodium hydroxide, etc., may be added.

An assembly of regenerated cellulose fibers on which a physiologically active substance is immobilized as described above can be used as a chemical reaction catalyst, a specific absorbent for separation and purification, a material for clinical examination, a medical material, and so forth.

An assembly of regenerated cellulose fibers on which an enzyme is immobilized as a physiologically active substance can be used as a chemical reaction catalyst. For example, a carrier with tyrosinase immobilized thereon can be used in the preparation of L-DOPA, a carrier with amylase or cellulose immobilized thereon can be used in the preparation of glucose, a carrier with aspartase immobilized thereon can be used in the preparation of L-aspartic acid, a carrier with acetatekinase or carbamatekinase immobilized thereon can be used in the reproduction of ATP, and a carrier with glucose isomerase immobilized thereon can be used in the preparation of fruit sugar.

An assembly of regenerated cellulose fibers on which a physiologically active substance is immobilized can be used as a specific absorbent for separation and purification. For example, a carrier with an enzyme immobilized thereon can be used in the separation and purification of coenzymes and enzyme inhibitors, a carrier with a coenzyme or enzyme inhibitor immobilized thereon can be used in the separation and purification of enzymes, a carrier with a hormone immobilized thereon can be used in the separation and purification of hormone recepters, a carrier with an antigen immobilized thereon can be used in the separation and purification of antibodies, and a carrier with an antibody immobilized thereon can be used in the separation and purification antigens. These specific absorbents can further be used as clinical test materials for the enzyme immunoassay or radio immunoassay in the quantitative determination of thyroid gland-stimulating hormones, thyroid gland hormones, insulin, steroid hormones, human placental gonadotropin, angiotensine, α-fetoproteine ferritin and HBs antigen.

As shown in Table 1, various diseases can be treated by removing various noxious substances from the body fluid by the use of the above-described specific absorbents.

The carrier of the present invention with a physiologically active substance immobilized thereon can retain from 70 to 98% of the strength and the degree of elongation of the rengenerated cellulose used as a starting material. Thus it can be used sufficiently satisfactorily in various applications.

TABLE 1

| Application of Specific Absorbents for Treatment of Diseases | | |
|---|---|---|
| Substance Immobilized | Substance to be Removed | Objective Disease |
| Thyroglobulin | Anti-thyroglobulin antibody | Hashimoto disease |
| Thyroid gland microsome | Anti-thyroid gland microsome antibody | " |
| e Antibody | e antigen | Hepatitis B |
| HBs antibody | HBs antigen | " |
| Acetylcholine receptor | Anti-acetylcholine receptor | Myasthenia |
| Malpighian corpuscles basement membrane | anti-basement membrane antibody | Goodpasture symptoma |
| DNA | anti-DNA antibody | SLE (Systemic Lupus Erythematosus) |
| Complement Clq | immuno complex DMA | SLE |
| Rheumatoid factor | immuno complex | Chronic rheumatoid arthritis |
| " | degenerated immuno globulin | Chronic rheumatoid arthritis |
| " | aggregated immuno globulin | SLE |
| Cryo globulin lgM | immuno complex | Chronic rheumatoid arthritis |
| " | immuno complex degenerated immuno globulin | Chronic rheumatoid arthritis |
| " | aggregated-immuno globulin | SLE |
| Fc and/or C3b receptor | immuno complex | chronic rheumatoid arthritis |
| Fc and/or C3b | degenerated | chronic rheumatoid |

TABLE 1-continued

Application of Specific Absorbents for Treatment of Diseases

| Substance Immobilized | Substance to be Removed | Objective Disease |
|---|---|---|
| receptor | immuno globulin | arthritis |
| Fc and/or C3b receptor | aggregated immuno globulin | SLE |
| Deoxyribonuclease | DNA, DNA-anti DNA, antibody | SLE |
| Platelet membrance | anti-platelet antibody | spontaneous purpura a thrombopenia |
| Albumin | thyroxine, triodine thronine | hyperthyroidism |
| " | bilirubin, free tryptophane | liver failure |
| " | guanidine compound | kidney failure |
| " | digitoxin | intoxication |
| Haptoglobin | free hemoglobin | hemolytic anemia |
| Hemovexin | heme | " |
| Anti-transcortine antibody | corisol | Cushing's Syndrome |
| Anit-corisol antibody | " | " |
| Conglutinine | immuno complex | diffuse collagen disease, nephritis, SLE, etc. |
| Immuno conglutinine | " | diffuse collagen disease, nephritis, SLE, etc. |
| Methylated albumin | DNA, DNA-anti DNA antibody RNA, RNA-anti RNA antibody | diffuse collagen disease, nephritis, SLE, etc. |
| Actinomycine D | DNA, DNA-anti DNA antibody RNA, RNA-anti RNA antibody | |
| Apoceruloplasmin | copper ion | Copper-poisoning, hepatic tract disease, anemia, toxemia of pregnancy |
| Transferin | ferric ion | hemochromatosis |
| Anti-angiotensine antibody | angiortensine II | Malignant hypertension |
| ENA (phosphate buffer soluble nucleus antigen) | anti nucleus antibody | SLE, chronic rheumatoid arthritis |
| Sm antigen | anti nucleus antibody | SLE, chronic rheumatoid arthritis |
| Liponuclease protein | anti nucleus antibody | SLE, chronic rheumatoid arthritis |
| Deoxyribonuclease protein | anti nucleus antibody | SLE, chronic rheumatoid arthritis |

The carrier of the present invention is easy to handle and can provide high physiological activity. Thus it can be used in a wide variety of applications such as a chemical reaction catalyst, a specific absorbent for separation and purification, a material for clinical examination, and a medical material.

The present invention is described in greater detail with reference to the following examples and comparative examples.

EXAMPLE 1 AND COMPARATIVE EXAMPLES 1 AND 2

Nine grams of viscose rayon yarns (120 deniers per 50 filaments; filament length: 5 centimeters) were dipped in 100 milliliters of a 4% by weight acetone solution of Gantrez AN169 (a maleic anhydride/methyl vinyl ether copolymer, manufactured by GAF Co.) and treated at 40° C. for 24 hours. After the treatment, the yarns were washed with acetone and then with hot water to thoroughly remove the excess Gantrez AN169, and then were vacuum dried at 110° C. for 10 hours, whereupon a carrier for immobilization of physiologically active substances was obtained. The acid anhydride group content per gram of the carrier (calculated as carboxyl group content by the neutralization titration process) was about 0.5 milliequivalent.

One gram of the above-prepared carrier was dipped in 10 milliliters of a 1% by weight phosphate buffer of anti-B type hepatitis human immunoglobulin (HBs antibody) (1/10M, pH 8.0) at 7° C. for 24 hours and then fully washed with a physiological saline solution. Two hundred milligrams of the carrier with the HBs antibody immobilized thereon was packed in a 1-milliliter volume column through which 2 milliliters of blood plasma (HBs antigen value $1:2^8$ was passed. After the filtration, the amount of blood plasma antigen dropped to $1:2^2$. Subsequently 2 milliliters of blood plasma ($1:2^8$) was passed four times through the column. After the filtration, the amount of blood plasma antigen dropped to $1:2^2$.

For comparison, powdered cellulose was treated with the Gantrez AN169 solution and subsequently reacted with the HBs antibody in the same manner as in the viscose rayon filament yarn. Two hundred milligrams of the cellulose with the HBs antibody immobilized thereon was packed in a 1-milliliter column through which 2 milliliters of blood plasma (HBs antigen value: $1:2^8$) was passed. After the passage, the amount of blood plasma antigen dropped to $1:2^2$.

Subsequently, 2 milliliters of blood plasma (HBs antigen value: $1:2^8$) was passed four times through the column. After the second passage, the amount of antigen was $1:2^2$, and after the third, fourth and fifth passages, it was $1:2^3$.

Furthermore, for comparison, 9 grams of the same viscose rayon yarns as used in Example 1 were treated in 164 grams of a mixed solvent of 17.3% by weight methanol, 13.7% by weight water and 69% by weight 2-propanol containing 2.7 grams of sodium hydroxide and, thereafter, 4.2 grams of monochloroacetic acid was added thereto and the yarns were treated at 70° C. for 3 hours to introduce thereinto carboxymethyl groups. After the reaction, the reaction mixture was cooled and treated with hydrochloric acid. Then the rayon yarns with carboxymethyl groups introduced thereinto were washed repeatedly with water until the pH was 3 or more and then dried whereupon there was obtained a carboxymethylated carrier for immobilization of physiologically active substances. Two hundred milligrams of the above-prepared carrier was packed in a 1-milliliter volume column through which 2 milliliters of blood plasma (HBs antigen value: $1:2^8$) was passed. After the passage, the amount of blood plasma antigen dropped to $1:2^4$.

Subsequently, 2 milliliters of blood plasma (HBs antigen value: $1:2^8$) was passed four times through the column. At the second and third passages, the amount of antigen was $1:2^4$, at the fourth and fifth passages, it was $1:2^5$.

The HBs antigen value was measured according to the method described in Kanai and Kanai ed., RINSHO KENSA GAIYO, 28th ed. (revised ed.), published by Kanehara Shuppan Co., Ltd., XX-40.

EXAMPLE 2

A carrier for immobilization of physiologically active substances was prepared in the same manner as in Example 1 except that acetone was replaced by cyclohexanone and the yarns were treated at 100° C. in the place of 40° C. The acid anhydride group content per gram of the carrier was about 2.4 milliequivalents (calculated as carboxyl group).

EXAMPLE 3

Ten grams of cuprammonium rayon yarns (100 deniers per 100 filaments, filament length 3 cm) were dipped in 100 milliliters of a 10% by weight methyl ethyl ketone solution of SMA 3000 (a maleic anhydride/styrene copolymer, manufactured by ARCO Chemical Co.) and treated at 60° C. for 36 hours. After the treatment, the yarns were washed with methyl ethyl ketone and then with acetone to thoroughly remove the excess SMA 3000, and thereafter the yarns were vacuum dried at 110° C. for 10 hours to prepare a carrier for immobilization of physiologically active substances. The acid anhydride group content per gram of the carrier was about 0.04 milliequivalent (calculated as carboxyl group).

EXAMPLE 4

A carrier for immobilization of physiologically active substances was prepared in the same manner as in Example 3 except that a methyl ethyl ketone solution of a maleic anhydride/ethylene copolymer was used in place of the methyl ethyl ketone solution of SMA 3000. The acid anhydride content per gram of the carrier was about 0.03 milliequivalent (calculated as carboxyl group).

EXAMPLE 5

A 10 centimeter×10 centimeter fabric made of viscose rayon filament (120 deniers per 50 filaments, using filaments of singly filament fineness of 2.4 deniers, filament length 4 cm) was dipped in 100 milliliters of a 2% by weight acetone solution of Gantrez AN169 (a maleic anhydride/methyl vinyl ether copolymer, manufactured by GAF Co.) and treated at 50° C. for 24 hours. Thereafter the fabric was washed with acetone and then with hot water, and then vacuum dried at 110° C. for 8 hours to prepare a carrier for immobilization of physiologically active substances. The acid anhydride group content per gram of the carrier was 0.4 milliequivalent (calculated as carboxyl group).

The above-prepared carrier was dipped in 100 milliliters of a phosphate buffer containing urokinase (pH 7.0, 1/10M, 2000 unit/ml) for 24 hours, and was then well washed with a physiological saline solution.

Measurement of the fibrinolytic activity was done according to the method described in Kanai and Kanai, ed., *RINSHO KENSAHO GAIYO*, 28th ed. (revised ed.), published by Kanehara Shuppan Co., Ltd., VI-105. That is, a fibrin plate was prepared by the described method, a circular fabric piece (diameter: 1 centimeter) was placed thereon, and dissolution of the fibrin was examined. After 24 hours, it was found that the fibrin was dissolved over a 3.5 centimeter-wide zone around the fabric.

While the invention has been described in detail and with reference to specific embodiments thereof, it will be apparent to one skilled in the art that various changes and modifications can be made therein without departing from the spirit and scope thereof.

What is claimed is:

1. A carrier for immobilization of physiologically active substances which is prepared by treating an assembly of regenerated cellulose fibers having a single fiber fineness of from 0.5 to 30 deniers and a length of at least 1 millimeter with a solution of a polymer having an acid anhydride group.

2. A carrier as in claim 1, wherein the single fiber fineness is from 1 to 20 deniers.

3. A carrier as in claim 1, wherein the length is at least 5 millimeters.

4. A carrier as in claim 1, wherein the acid anhydride group content per gram of the carrier (calculated as carboxyl group) is from 0.0002 to 20 milliequivalents.

5. A carrier as in claim 1, wherein the single fiber fineness is from 1 to 20 deniers, the length is at least 5 millimeters, and the acid anhydride group content per gram of the carrier (calculated as carboxyl group) is from 0.0002 to 20 milliequivalents.

6. A carrier as in claim 1, wherein the length is at least 20 millimeters.

7. A carrier as in claim 5, wherein the length is at least 20 millimeters.

8. A carrier as in claim 1, wherein the polymer having an acid anhydride group is a poly(carboxylic anhydride) or a copolymer thereof.

9. A carrier as in claim 8, wherein the copolymer is copolymers of maleic anhydride and aliphatic vinyl ethers, copolymers of maleic anhydride and olefin monomers, copolymers of maleic anhydride and aromatic vinyl monomers and copolymers of maleic anhydride and aliphatic vinyl esters.

10. A carrier as in claim 9, wherein the copolymer is selected from the group consisting of a maleic anhydride/methyl vinyl ether copolymer, a maleic anhydride/ethyl vinyl ether copolymer, a maleic anhydride/butanediol divinyl ether copolymer, a maleic anhydride/ethylene copolymer, a maleic anhydride/propylene copolymer, a maleic anhydride/isobutylene copolymer, a maleic anhydride/styrene copolymer, and a maleic anhydride/vinyl acetate copolymer.

11. A carrier as in claim 8, wherein the poly(carboxylic anhydride) is selected from the group consisting of poly(maleic anhydride), poly(itaconic anhydride), poly(acrylic anhydride) and poly(methacrylic anhydride).

12. A carrier as in claim 1, wherein the polymer having an acid anhydride group is dissolved in one or more solvents selected from the group consisting of methanol, ethanol, propanol, isopropanol, butanol, tetrahydrofuran, ethyl acetate, methyl acetate, benzaldehyde, formaldehyde, acetone, cyclohexanone, methyl ethyl ketone, mesytil oxide, diacetone alcohol, 2-pyrrolidone, N-methyl-2-pyrrolidone, N-vinyl-2-pyrrolidone, butyralactone, acetic acid, dimethylformamide, and pyridine.

13. A carrier as in claim 12, wherein the concentration of the polymer having an acid anhydride group is from 0.1 to 30% by weight based on the weight of the solution.

14. A carrier as in claim 12, wherein the concentration of the polymer having an acid anhydride group is from 0.5 to 10% by weight based on the weight of the solution.

15. A carrier as in claim 1, wherein the assembly of regenerated cellulose fibers is treated with the solution at a temperature of from 0° to 150° C.

16. A carrier as in claim 1, wherein the assembly of regenerated cellulose fibers is treated with the solution at a temperature of from 0° to 100° C.

17. A carrier as in claim 1, wherein the assembly of regenerated cellulose fibers is treated with the solution at a temperature of from 20° to 80° C.

18. A carrier as in claim 1, wherein the treatment of the assembly of regenerated cellulose fibers with the solution is carried out for period of from about 10 minutes to 72 hours.

19. A carrier as in claim 1, wherein the treatment of the assembly of regenerated cellulose fibers with the solution is carried out for period of from about 30 minutes to 36 hours.

20. A carrier as in claim 1, wherein the acid anhydride group content per gram of the carrier (calculated as carboxyl group) is from 0.002 to 10 milliequivalents.

21. A carrier as in claim 1, wherein the acid anhydride group content per gram of the carrier (calculated as carboxyl group) is from 0.02 to 5 milliequivalents.

* * * * *